United States Patent [19]

Hocquaux et al.

[11] Patent Number: 4,895,575
[45] Date of Patent: Jan. 23, 1990

[54] USE OF 5-HYDROXYNAPHTHOQUINONES FOR DYEING HUMAN KERATIN FIBRES

[75] Inventors: Michel Hocquaux, Paris; Jean Cotteret, Limay; Georges Rosenbaum, Asnieres, all of France

[73] Assignee: L'Oreal, Paris, France

[21] Appl. No.: 210,506

[22] Filed: Jun. 23, 1988

Related U.S. Application Data

[63] Continuation of Ser. No. 557,963, Dec. 5, 1983, abandoned.

[30] Foreign Application Priority Data

Dec. 8, 1982 [LU] Luxembourg ............ 84.511

[51] Int. Cl.$^4$ .................................................. A61K 7/13
[52] U.S. Cl. ............................................ 8/424; 8/405; 8/406; 8/428; 8/429; 8/663
[58] Field of Search ............... 8/405, 428, 429, 663, 8/424, 406

[56] References Cited

U.S. PATENT DOCUMENTS

| | | | |
|---|---|---|---|
| 3,041,244 | 6/1962 | Feit et al. | 8/408 |
| 3,272,713 | 9/1966 | Runge | 424/59 |
| 3,516,778 | 6/1970 | Brunner | 8/405 |
| 4,358,286 | 11/1982 | Grollier et al. | 8/428 |

FOREIGN PATENT DOCUMENTS

| | | |
|---|---|---|
| 2473310 | 7/1981 | France . |
| 889813 | 2/1962 | United Kingdom . |
| 892191 | 3/1962 | United Kingdom . |
| 2065177 | 6/1981 | United Kingdom . |

OTHER PUBLICATIONS

CA 91:13716h, Kondo et al, 1977.
CA 91:71707a, Kondo et al, 1979.
Thomson, *Naturally Occurring Quinones*, 1971 Academic Press, NY, pp. 221–230.
Chemical Abstracts, vol. 66, CA No. 101462v (Vlad et al) 1967.
"Studies in Mass Spectrometry I. Mass Spectra of Substituted Naphthoquinones", Bowie et al, J.A.C.S., pp. 5094–5099, Nov. 1965.

*Primary Examiner*—Paul Lieberman
*Assistant Examiner*—Linda D. Skaling
*Attorney, Agent, or Firm*—Cushman, Darby & Cushman

[57] ABSTRACT

The invention relates to the use of 5-hydroxy-1,4-naphthoquinones of the formula:

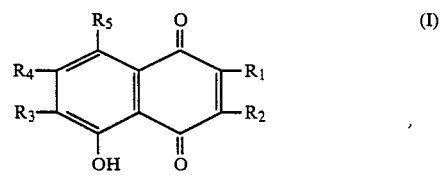

in which $R_1$ and $R_2$, which are identical or different, independently of one another denote a hydrogen atom, a methyl, methoxy or nitro group or a halogen atom; $R_3$ and $R_4$, which are identical or different, independently of one another denote a hydrogen atom or a hydroxyl, methyl or methoxy group; and $R_5$ denotes a hydrogen atom or a methyl or methoxy group, with the proviso that at least one of the substituents $R_1$ and $R_2$ is different from hydrogen, if $R_3$, $R_4$ and $R_5$ simultaneously denote a hydrogen atom, for dyeing human keratin fibres, in particular the hair.

11 Claims, No Drawings

USE OF 5-HYDROXYNAPHTHOQUINONES FOR DYEING HUMAN KERATIN FIBRES

This is a continuation of application Ser. No. 06/557,963, filed Dec. 5, 1983, abandoned.

The present invention relates to the use of 5-hydroxynaphthoquinones for dyeing human keratin fibres, in particular the hair, and to the processes and dyeing compositions in which these dyestuffs are used.

In the field of hair dyeing, it is common to use numerous direct dyestuffs such as triarylmethane dyestuffs, nitro derivatives of the benzene series, indoamines, aminoanthraquinones, xanthenes, acridines and azo dyestuffs.

Certain hydroxynaphthoquinone dyestuffs have also been used for direct dyeing of the hair. In this respect, there may be mentioned, more particularly, lawsone (2-hydroxy-1,4-naphthoquinone), which is the colouring principle of henna, naphthazarine (5,8-dihydroxy-1,4-naphthoquinone) and juglone (5-hydroxy-1, 4-naphthoquinone), which is the colouring principle of walnut.

We have disclosed in British Patent Application No. 82. 34179 the use of certain 2-hydroxynaphthoquinones for dyeing human keratin fibres. However, none of these dyestuffs gives green-brown, green or green-yellow colourations, or corresponds to a hue notation (H) of 2.5 Y to 5 GY according to Munsell's system of notation. These tints are particularly necessary for obtaining natural hues or hues with golden highlights.

Juglone, whose tinctorial strength is in the right range of hues, has the disadvantage that its resistance to oxidation is too low.

We have therefore sought other hydroxynaphthoquinones possessing a good tinctorial strength and a low sensitivity to oxidation, as a result of which a particular class of 5-hydroxy-1, 4-naphthoquinones has been found. In particular, these dyestuffs generally possess a lower sensitivity to oxidation than juglone and a very good affinity for keratin fibres, resulting in a high tinctorial strength.

Furthermore, these dyestuffs have a good resistance to degrading agents, such as washing agents, and have improved stability to pH variations, compared with the known naphthoquinone dyestuffs.

Finally, these dyestuffs make it possible to obtain a range of hues which, expressed in Munsell's system of notation, is from 2.5 Y to 5 GY, in particular in an acid medium.

The present invention therefore relates to the use of a new class of 5-hydroxy-1,4-naphthoquinones for dyeing human keratin fibres. Accordingly the present invention provides dyeing processes in which these compounds are used, and also dyeing compositions in which they are present, together with a cosmetically acceptable carrier or diluent.

The 5-hydroxy-1,4-naphthoquinones used according to the invention correspond to the following general formula:

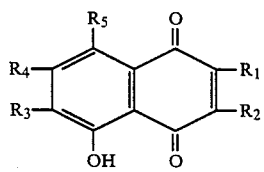

in which $R_1$ and $R_2$, which are identical or different, denote a hydrogen atom, a methyl, methoxy or nitro group or a halogen atom.

$R_3$ and $R_4$, which are identical or different, denote a hydrogen atom, a hydroxyl group or a methyl or methoxy group.

$R_5$ denotes a hydrogen atom or a methyl or methoxy group, with the proviso that at least one of the substituents $R_1$ and $R_2$ is different from hydrogen if $R_3$, $R_4$ and $R_5$ simultaneously denote a hydrogen atom.

The dyestuffs which are more particularly preferred according to the invention are the following compounds: 2-methyl-5-hydroxy-1,4-naphthoquinone, 2-methyl-3-chloro-5-hydroxy-1,4-naphthoquinone, 2-methoxy-5-hydroxy-1,4-naphthoquinone and 3-methoxy-5-hydroxy-1,4-naphthoquinone.

Other dyestuffs which correspond to the above formula and are of value within the scope of the invention include the following: 3-methyl-5-hydroxy-1,4-naphthoquinone, 6-methyl-5-hydroxy-1,4-naphthoquinone, 7-methyl-5-hydroxy-1,4-naphthoquinone, 8-methyl-5-hydroxy-1,4-naphthoquinone, 2-chloro-5-hydroxy-1,4-naphthoquinone, 3-chloro-5-hydroxy-1,4-naphthoquinone, 2,3-dichloro-5-hydroxy-1,4-naphthoquinone, 5,7-dihydroxy-1,4-naphthoquinone, 5,6-dihydroxy-1,4-naphthoquinone, 2-chloro-5,7-dihydroxy-1,4-naphthoquinone, 2,3-dimethyl-5,7-dihydroxy-1,4-naphthoquinone, 2-methoxy-7-methyl-5-hydroxy-1,4-naphthoquinone, 3-methoxy-7-methyl-5-hydroxy-1,4-naphthoquinone and 2-methyl-6-methoxy-5-hydroxy-1,4-naphthoquinone.

The dyestuffs of the above formula can be used as obtained by synthesis or, if appropriate, in the form of products obtained from organisms producing them or of plants containing them, in the case of dyestuffs of natural origin. In the latter case, the products containing these dyestuffs can be used either in the form of extracts or in the form of homogenisates of all or part of organisms or plants.

The dyeing compositions for human keratin fibres according to the invention are essentially characterised in that they contain at least one dyestuff corresponding to the formula (I) above, in a cosmetically acceptable medium suitable for dyeing these fibres.

The dyestuffs are preferably present in these compositions in proportions from 0.01 to 5% by weight and preferably from 0.1 to 3% by weight, expressed as active dyeing ingredient relative to the total weight of the composition.

The specified dyestuffs can be used individually or in a mixture, in liquid compositions of varying degrees of thickness, or in compositions presented in the form of, for example, gels or oils, or in powders to be diluted with a liquid at the time of use.

These dyestuffs can be used in combination with other direct dyestuffs. A preferred form of the invention is the use of dyestuffs of the formula (I) in conjunction with natural dyestuffs such as lawsone or powdered henna leaves.

In the latter case, a particularly preferred embodiment of the compositions according to the invention consists of a poultice. In this embodiment, the 5-hydroxy-1,4-naphthoquinone of natural origin capable of adopting the various forms mentioned above may be prepared in the form of a powder which is stable on storage, and introduced into a solid medium, which can be composed of a powder, flour or starchy or mucilaginous substance, and this is diluted at the time of use with an appropriate liquid so as to form a mixture having a consistency suitable for application to the hair.

The powders used in this type of composition commonly referred to as a "poultice" may be insoluble substances such as silicas, plants, clays, plants powdered after solvent extraction of their active principles, or alternatively plants or animals containing the 5-hydroxy-1,4-naphthoquinones according to the invention. The liquid used to dilute the powder may be water and/or a cosmetically acceptable solvent such as an alcohol, glycol or oil. The viscosity generally obtained after mixing varies from 300 to 5,000 centipoises.

In the other embodiments, the cosmetically acceptable medium is aqueous and has a pH which is suitably from 2 to 11 and preferably from 2 to 7; the pH can be adjusted to the desired value using alkalising agents or acidifying agents well known in this field.

These compositions can also contain anionic, cationic, non-ionic or amphoteric surface-active agents or mixtures thereof. Amongst the preferred surface-active agents, there may be mentioned, in particular, soaps, alkylbenzenesulphonates, alkylnaphthalenesulphonates, fatty alcohol sulphates, oxyethyleneated sulphates or sulphonates, guaternary ammonium salts, fatty acid diethanolamides, polyoxyethyleneated or polyglycerolated acids, alcohols or amides and polyoxyethyleneated or polyglycerolated alkylphenols. The surface-active agents are suitably present in the compositions according to the invention in an amount of from 0.1 to 55% by weight and preferably from 1 to 40% by weight, relative to the total weight of the composition.

These compositions can also contain organic solvents mixed with water; examples of these organic solvents include lower alkanols such as ethanol and isopropanol, polyols such as glycerol, glycols or glycol ethers such as ethylene glycol, propylene glycol, ethylene glycol monobutyl ether and diethylene glycol monoethyl ether and monomethyl ether, and mixtures thereof. These solvents are preferably used in proportions from 1 to 60% by weight and more particularly from 3 to 30% by weight, relative to the total weight of the composition.

These compositions can also contain anionic, non-ionic, cationic or amphoteric polymers or mixtures thereof, generally in proportions of 0.1 to 5% by weight.

These compositions can be thickened, preferably with sodium alginate, gum arabic, guar or carob gum, pectins, cellulose derivatives such as methylcellulose, hydroxymethylcellulose, hydroxypropylcellulose and carboxymethylcellulose, and various polymers serving this purpose, such as polymers of acrylic acid derivatives. It is also possible to use inorganic thickeners such as bentonite. These thickeners are preferably present in proportions of between 0.1 to 5% by weight and in particular of between 0.5 to 3% by weight relative to the total weight of the composition.

It is of course possible to add to the compositions according to the invention any other adjuvant normally used in dyeing compositions for keratin fibres, in particular for human hair, such as penetrating agents, sequestering agents, antioxidants, buffers and perfumes.

If the compositions contain other direct dye-stuffs, these are suitably present in proportions from 0.005 to 10% by weight, relative to the total weight of the composition.

The process for dyeing human keratin fibres, in particular human hair, according to the invention is essentially characterised in that at least one composition as defined above is applied to the human keratin fibres, in particular to the hair, before or after shampooing, it is left on the fibres for, say, 5 to 60 minutes, and preferably 5 to 40 minutes, and the said fibres are rinsed and dried. A composition in the form of a setting lotion, in this case containing polymers defined above, can also be applied to the hair after shampooing, and the hair is then dried.

Of course, another form of the process consists of the application of a poultice as defined above.

The dyeing of human keratin fibres, in particular of the hair, can also be carried out by multistep processes, at least one of these steps consisting in applying a dyestuff of the formula (I) by means of one of the compositions defined above. These multistep processes make it possible, in particular, to use compositions having different pH values according to the nature of the dyestuffs present.

The following Examples further illustrate the present invention.

EXAMPLE 1

The following dyeing composition is prepared:

| | | |
|---|---|---|
| 2-Methoxy-5-hydroxy-1,4-naphthoquinone | | 0.5 g |
| Cetyl alcohol | | 17 g |
| Cetyl-stearyl alcohol containing 15 mol of ethylene oxide, sold by HENKEL under the name MERGITAL CS 15 E | | 6 g |
| Oleyl alcohol | | 3 g |
| Citric acid q.s. | pH | 3.2 |
| Distilled water q.s. | | 100 g |

This composition is in the form of a cream which is applied to blond hair for 30 minutes. After rinsing and drying, the hair is coloured a dull golden blond hue.

EXAMPLE 2

The following dyeing composition is prepared:

| | | |
|---|---|---|
| 2-methyl-3-chloro-5-hydroxy-1,4-naphthoquinone | | 0.05 g |
| 2-N—(β-hydroxyethyl)-amino-5-(β-hydroxyethoxy)-nitrobenzene | | 0.05 g |
| 90/10 vinylpyrrolidone/crotonic acid copolymer | | 1.8 g |
| 60/40 vinylpyrrolidone/vinyl acetate copolymer | | 0.4 g |
| Ethyl alcohol q.s. | | 50° alcoholic strength |
| Triethanolamine q.s. | pH | 6 |
| Distilled water q.s. | | 100 g |

This setting lotion is applied to deep blond hair. The hair is dried. It then has golden coppery highlights.

EXAMPLE 3

The following dyeing composition is prepared:

| | | |
|---|---|---|
| 2-methyl-5-hydroxy-1,4-naphthoquinone | | 0.05 g |
| 5,7-dihydroxy-1,4-naphthoquinone | | 0.05 g |
| 2-N—methylamino-5-N,N—bis-(β-hydroxyethyl)-aminonitrobenzene | | 0.15 g |
| 2-amino-4-methyl-5-hydroxynitrobenzene | | 0.05 g |
| Monohydrate of the sodium salt of 1,2-dihydroxyanthraquinone-3-sulphonic acid | | 0.05 g |
| Sodium salt of sulphated oxyethyleneated alkanol containing 0.6 meq/g, sold under the name SACTIPON 8533 by LEVER | | 20 g |
| Ethylglycol | | 10 g |
| Lactic acid q.s. | pH | 4 |
| Distilled water q.s. | | 100 g |

This shampoo base is used for dyeing chestnut hair. It is left on the hair for 30 minutes and the hair is rinsed and dried. The hair then possesses golden brown highlights.

EXAMPLE 4

The following dyeing composition is prepared:

| | | |
|---|---|---|
| 2-methyl-5-hydroxy-1,4-naphthoquinone | | 0.4 g |
| 3-methoxy-5-hydroxy-1,4-naphthoquinone | | 0.05 g |
| 2-N—(β-hydroxyethyl)-amino-5-hydroxynitrobenzene | | 0.3 g |
| Cetyl alcohol | | 17 g |
| Cetyl-stearyl alcohol containing 15 mol of ethylene oxide, sold by HENKEL under the name MERGITAL CS 15 E | | 6 g |
| Oleyl alcohol | | 3 g |
| Citric acid q.s. | pH | 3.5 |
| Distilled water q.s. | | 100 g |

This cream is applied for 30 minutes to chestnut hair. After rinsing and drying, the hair has intense coppery red highlights.

EXAMPLE 5

The following dyeing composition is prepared:

| | | |
|---|---|---|
| 5,7-dihydroxy-1,4-naphthoquinone | | 0.05 g |
| Dyestuff of Colour Index No. 42555, sold by PCUK | | 0.005 g |
| Isolane Black KR 150%, sold by BAYER | | 0.05 g |
| Dyestuff of Colour Index No. 45170, sold by KOHNSTAMM | | 0.02 g |
| 90/10 vinylpyrrolidone/crotonic acid copolymer | | 1.8 g |
| 60/40 vinylpyrrolidone/vinyl acetate copolymer | | 0.4 g |
| Ethyl alcohol q.s. | | 50° alcoholic strength |
| Triethanolamine q.s. | pH | 6 |
| Distilled water q.s. | | 100 g |

This setting lotion is applied to deep chestnut hair. After drying, the hair possesses purple-violet mahogany highlights.

EXAMPLE 6

The following dyeing composition is prepared:

| | |
|---|---|
| 2-methyl-3-chloro-5-hydroxy-1,4-naphthoquinone | 0.5 g |
| 2-methyl-5-hydroxy-1,4-naphthoquinone | 1 g |
| 2-hydroxy-1,4-naphthoquinone | 0.5 g |
| Powdered residue from extracted saponaria | 35 g |
| Powdered maize cobs | 15 g |
| Citric acid | 4 g |
| Vidogum L175 sold by UNIPECTINE | 3 g |
| Low-fat milk powder q.s. | 100 g |

This solid composition is treated with three times its own weight of warm water. The poultice thus obtained is applied to light chestnut hair. After an interval of 30 minutes, the hair is rinsed and dried. The hair is then embellished with golden highlights.

We claim:

1. A composition for dyeing human hair comprising in a carrier suitable for application to said human hair a naphthoquinone of the formula

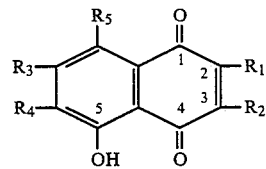

wherein
$R_1$ and $R_2$ each independently represent hydrogen, methyl, methoxy, nitro or halogen,
$R_3$ and $R_4$ each independently represent hydrogen, methyl or methoxy and
$R_5$ represents hydrogen, methyl or methoxy, with the proviso that at least one of $R_1$ and $R_2$ is other than hydrogen when $R_3$, $R_4$ and $R_5$ are simultaneously hydrogen, said naphthoquinone being present in an amount effective to dye said hair, said composition also containing at least one of an anionic, cationic, nonionic, or amphoteric surface active agent or polymer, or a solid powdered medium selected from the group consisting of silica, a plant other than a plant containing said naphthoquinone, clay, flour, a starchy or mucilagenous substance, and a plant powdered after solvent extraction of the active substance.

2. The composition of claim 1 wherein $R_1$ and $R_2$ each represent hydrogen, $R_3$ and $R_4$ each independently represent hydrogen, chlorine or methoxy and $R_5$ represents methyl or methoxy.

3. The composition of claim 1 wherein said naphthoquinone is present in an amount from 0.01 to 5 percent by weight, expressed as active dyeing ingredients, relative to the total weight of said composition.

4. The composition of claim 1 wherein said carrier is an aqueous carrier and said composition has a pH ranging from 2 to 11.

5. The composition of claim 4 wherein said composition has a pH ranging from 2 to 7.

6. A process for dyeing human hair comprising applying to said hair the composition of claim 1, permitting said composition to remain in contact with the hair for 5 to 60 minutes and rinsing said hair.

7. The process of claim 6 which includes drying the resulting rinsed hair.

8. A composition for dyeing human hair comprising in a carrier suitable for application to said human hair a naphthoquinone selected from the group consisting of 2-methyl-5-hydroxy-1,4-naphthoquinone, 2-methyl-3-chloro-5-hydroxy-1,4-naphthoquinone, 2-methoxy-5-hydroxy-1,4-naphthoquinone and 3-methoxy-5-hydroxy-1,4-naphthoquinone, said naphthoquinone being present in an amount effective to dye said hair, said composition also containing at least one of an anionic, cationic, nonionic, or amphoteric surface active agent or polymer, or a solid powdered medium selected from the group consisting of silica, a plant other than a plant containing said naphthoquinone, clay, flour, a starchy or mucilagenous substance, and a plant powdered afte solvent extraction of the active substance.

9. The composition of claim 8 wherein said naphthoquinone is present in an amount ranging from 0.01 to 5 percent by weight, expressed as active dyeing ingredient, relative to the total weight of said composition.

10. A composition for dyeing human hair comprising in a carrier suitable for application to said human hair a naphthoquinone selected from the group consisting of 3-methyl-5-hydroxy-1,4-naphthoquinone, 6-methyl-5-hydroxy-1,4-naphthoquinone, 7-methyl-5-hydroxy-1,4-naphthoquinone, 8-methyl-5-hydroxy-1,4-naphthoquinone, 2-chloro-5-hydroxy-1,4-naphthoquinone, 3-chloro-5-hydroxy-1,4-naphthoquinone, 2,3-dichloro-5-hydroxy-1,4-naphthoquinone, 2-chloro-5,7-dihydroxy-1,4-naphthoquinone, 2,3-dimethyl-5,7-dihydroxy-1,4-naphthoquinone, 2-methoxy-7-methyl-5-hydroxy-1,4-naphthoquinone, 3-methoxy-7-methyl-5-hydroxy-1,4-naphthoquinone and 2-methyl-6-methoxy-5-hydroxy-1,4-naphthoquinone, said naphthoquinone being present in an amount effective to dye said hair, said composition also containing at least one of an anionic, cationic, nonionic, or amphoteric surface active agent or polymer, or a solid powdered medium selected from the group consisting of silica, a plant other than a plant containing said naphthoquinone, clay, flour, a starchy or mucilagenous substance, and a plant powdered after solvent extraction of the active substance.

11. The composition of claim 10 wherein said naphthoquinone is present in an amount ranging from 0.01 to 5 percent by weight, expressed as active dyeing ingredient, relative to the total weight of said composition.

* * * * *